United States Patent [19]

Aichinger et al.

[11] Patent Number: 4,907,252
[45] Date of Patent: Mar. 6, 1990

[54] MEDICAL EXAMINATION SYSTEM WITH GENERATION OF THE INTERNAL PATIENT IMAGE CONTROLLED BY A SURFACE IMAGE OF THE PATIENT

[75] Inventors: Horst Aichinger, Fuerth; Hans-Juergen Gerlach, Erlangen, both of Fed. Rep. of Germany

[73] Assignee: Siemens Aktiengesellschaft, Berlin and Munich, Fed. Rep. of Germany

[21] Appl. No.: 302,683

[22] Filed: Jan. 27, 1989

[30] Foreign Application Priority Data

Apr. 27, 1988 [DE] Fed. Rep. of Germany ....... 3814246

[51] Int. Cl.[4] .............................................. H05G 1/64
[52] U.S. Cl. ......................................... 378/99; 378/63; 378/151; 378/205; 378/206; 128/653 R; 324/309
[58] Field of Search .......................... 378/99, 145–146, 378/63, 150–153, 195, 205–206, 209; 128/653, 654, 660.07; 324/309, 318

[56] References Cited

U.S. PATENT DOCUMENTS

| | | | |
|---|---|---|---|
| 4,118,631 | 10/1978 | Froggatt | 378/205 |
| 4,173,970 | 11/1979 | Momin | 128/736 |
| 4,262,306 | 4/1981 | Renner | 378/100 |
| 4,609,940 | 9/1986 | Born et al. | 358/111 |
| 4,791,934 | 12/1988 | Brunnett | 378/205 |
| 4,831,645 | 5/1989 | Guenther et al. | 378/205 |

FOREIGN PATENT DOCUMENTS

| | | |
|---|---|---|
| 2361155 | 6/1975 | Fed. Rep. of Germany . |
| 2017450 | 3/1979 | Fed. Rep. of Germany . |
| 3436444 | 4/1986 | Fed. Rep. of Germany . |

OTHER PUBLICATIONS

"New Product" section from Automatisierungstechnische Praxis, vol. II, 1988, p. 99.

Primary Examiner—Craig E. Church
Assistant Examiner—John C. Freeman
Attorney, Agent, or Firm—Hill, Van Santen, Steadman & Simpson

[57] ABSTRACT

A medical examination system includes components for generating an internal image of a patient, such as an x-ray image, and components for generating an image of the external surface of at least a portion of the patient. The signals obtained from the surface scan of the patient are used to control the positioning of other components, such as the patient support and/or the primary radiation diaphragm. The internal and surface images can be compared to achieve precise positioning of the patient and/or a setting of the primary radiation diaphragm to avoid blooming.

11 Claims, 3 Drawing Sheets

MEDICAL EXAMINATION SYSTEM WITH GENERATION OF THE INTERNAL PATIENT IMAGE CONTROLLED BY A SURFACE IMAGE OF THE PATIENT

BACKGROUND OF THE INVENTION

1. Field of the Invention

The present invention is directed to a medical examination system including means for generating an internal image of a patient, and means for generating an image of the external surface of the patient, and in particular to such a system wherein signals from the latter means are used to control selected components in the former means.

2. Description of the Prior Art

Medical examination systems are known wherein internal images of a patient are produced using an x-ray diagnostics installation for positioning the patient, even if the examination system is not itself used to generate an x-ray image. Such systems include those for generating conventional x-ray shadow images, computer tomography, magnetic resonance imaging, and ultrasound imaging. The diagnosis made from an image assumes that a precise and accurate positioning of the patient has been undertaken prior to creating the image.

It is also known to produce x-ray transillumination images and surface images of an examination subject using two video cameras.

SUMMARY OF THE INVENTION

It is an object of the present invention to provide a medical examination system having means for generating an internal image of a patient, and means for generating an external, surface image of the patient, wherein the signals obtained from the surface scan of the patient are used to control the positioning of selected components in the means for generating the internal image.

The above and other objects are achieved in accordance with the principles of the present invention in a medical examination system wherein the means for generating an internal image has a memory to which the surface images of the patient are supplied, obtained from the surface scan. The means for generating an internal image also includes a comparator. The comparator generates an output signal for driving an adjustable component, such as the primary radiation diaphragm and/or the patient support. The output of the comparator is dependent upon the difference between the stored image of the patient, and a current patient image.

In addition to being used to obtain information about the patient for the examining personnel to complete the internal image of the patient, the surface image can also be used as a three-dimensional mask for re-positioning the patient in routine follow-up examinations. In medical technology, especially in radiology, such follow-up examinations are often necessary, which require that the patient be placed in precisely the same position as in a preceding examination. The surface image can be used to adjust the patient and the components, such as the patient support, to achieve such position repetition.

Precise reproduction of the same patient position as was used in a preceding exposure is required, for example, in subsequent exposures which are taken for the purpose of measuring the calcium content of bone substance in osteoporosis. This is because the percentage change of calcium content over time, i.e., over successive examinations, is on the order of magnitude of the reproduction precision of the measuring position. Although computer tomography x-ray images have been used as a positioning aid for this purpose, the use of a surface image in accordance with the principles of the present invention makes further improvement possible.

Another problem in the generation of internal patient images is that of blooming. Blooming occurs when the radiation is not properly gated onto the subject. This has two disadvantages. The first disadvantage is that the patient is exposed to higher than necessary radiation levels, due to scattered radiation. The second disadvantage is a loss in image quality.

The surface image generated in accordance with the principals of the present invention can be used to control the positioning of the primary radiation diaphragm to achieve an exact gating of the x-ray beam, thereby avoiding blooming.

DESCRIPTION OF THE PREFERRED EMBODIMENTS

Figure 1:
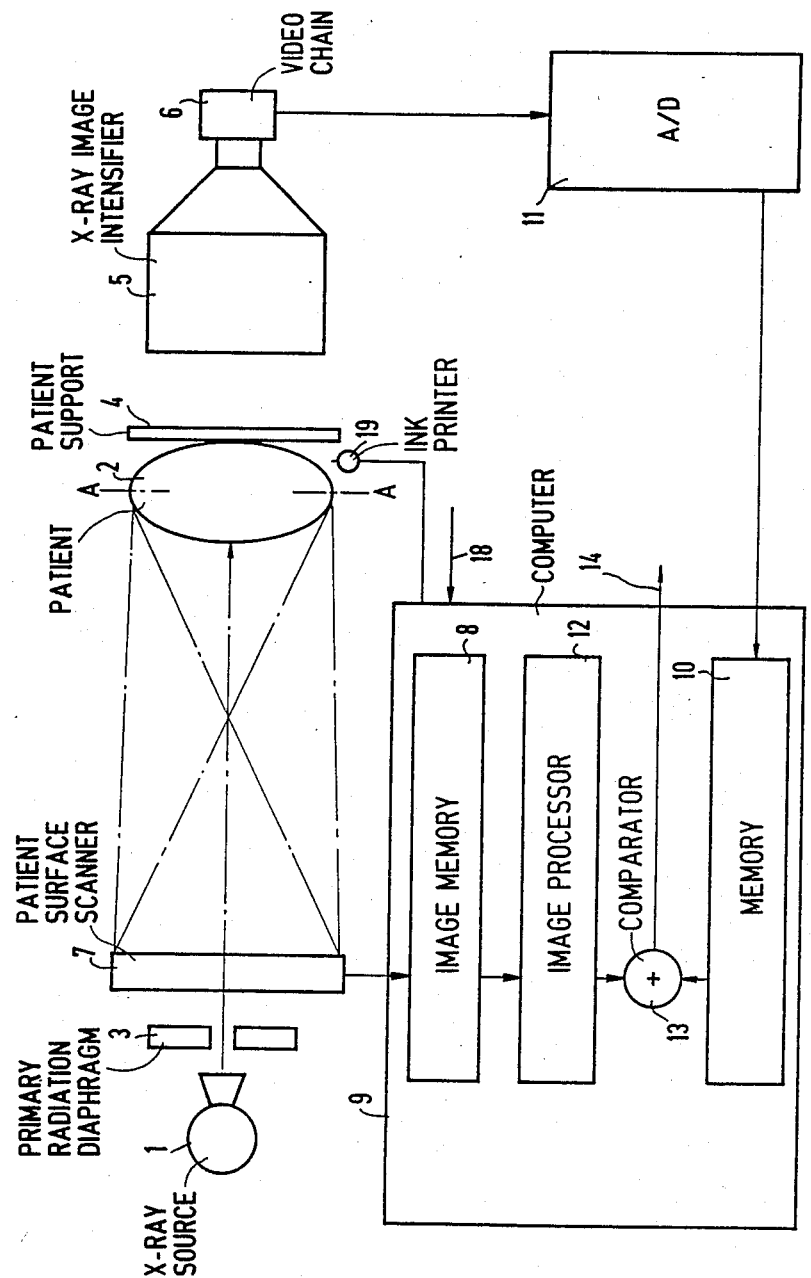
FIG. 1 is a schematic block diagram of a medical examination system constructed in accordance with the principles of the present invention.

As shown in FIG. 1, a medical examination system constructed in accordance with the principles of the present invention includes an x-ray source 1 which generates an x-ray beam which transirradiates a patient 2 (shown in cross-section) through a primary radiation diaphragm 3. The patient 2 lies on a patient support 4. Radiation attenuated by the patient 2 is incident on the input screen of an x-ray image intensifier 5, having an output screen connected to a video chain 6 in a known manner for producing x-ray shadow images.

A patient surface scanner 7, which may be a laser scanner, is disposed facing the patient 2 for producing a geometrical or topological scan of the surface of the patient 2. Various types of surface scanners suitable for use as the scanner 7 are known in the art. Electrical signals corresponding to the shape of the surface of the patient are formed from information identifying the scan direction and the scan angle.

A surface image generated by the scanner 7 is stored in a memory 8 of a computer 9. The computer 9 includes a further memory 10, which receives and stores the x-ray image from the video chain 6, via an analog-to-digital converter 11. An image computer 12 produces a contour image from the surface image in the memory 8, and supplies electrical signals corresponding to this contour image to a comparator 13. The comparator 13 also receives signals corresponding to the contours of the x-ray image stored in the memory 10. The comparator 13 generates a superposition image at its output 14. This superposition image permits a better diagnosis than is possible only on the basis of the x-ray shadow image from the video chain 6.

The video chain 6 generates an internal image of the patient. Such an image may also be acquired using another type of image-generating system, for example, a computer tomography system, a magnetic resonance imaging system, or an ultrasound imaging system. The scanner 7, instead of being a laser scanner, may be any suitable type of means for scanning the surface of the patient, for example, a system which produces such a surface image by acoustic emission.

Figure 2:
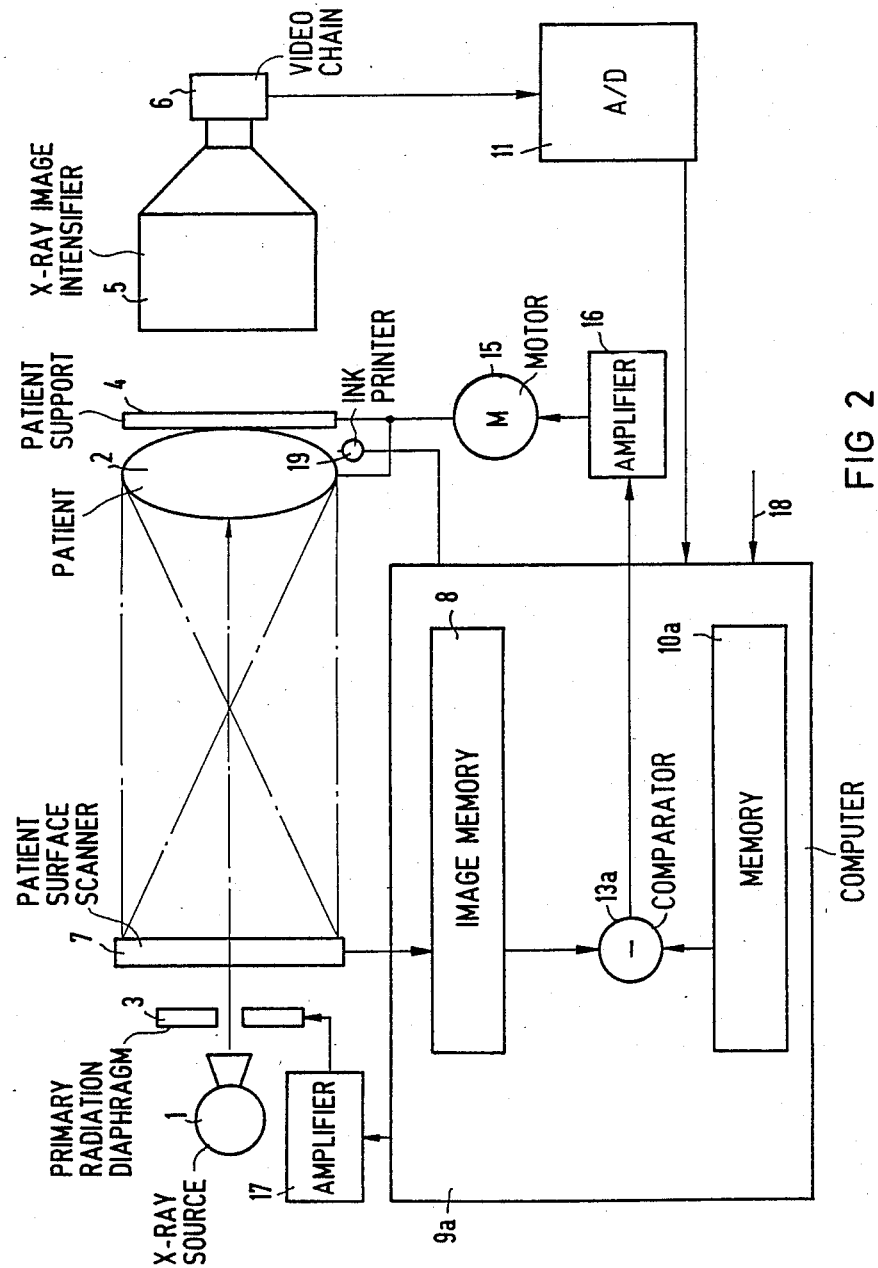
FIG. 2 is a schematic block diagram of another embodiment of a medical examination system constructed in accordance with the principles of the present invention.

A further embodiment of the system is shown in FIG. 2, wherein components identical to those already described in FIG. 1 are provided with the same reference symbols. In this embodiment, the memory 8 is contained in a computer 9a, which also contains a memory 10a for a three-dimensional surface image of the patient 2, obtained in an earlier examination. A comparator 13a compares the current surface image in the memory 8 to the earlier surface image in the memory 10a. The output of the comparator 13a controls a motor 15 via an amplifier 6, which adjusts the position of the patient support 4 until the two surface images coincide. At this point, the patient 2 is positioned as he or she was positioned in the earlier examination. Additionally, the computer 9a controls the size of the opening of the primary radiation diaphragm 3 via an amplifier 17 so that the x-ray beam from the x-ray source 1 is gated to be as small as possible without degrading the resulting image, i.e., the boundary or size of the radiation field is optimally approximated (matched) to the examined region of the patient 2. Blooming is substantially prevented by such control.

In addition to controlling the position of the patient 2 on the basis of the comparison of the current image in the memory 8 and the earlier image in the memory 10a, the position of the patient 2 via the motor 15 can also be undertaken by comparing the current image in the memory 8 with the current image from the output of the analog-to-digital converter 11. In this case, the motor 15 then adjusts the patient support 4 until the current surface image in the memory 8 substantially coincides with the earlier surface image in the memory 10a and, with respect to the contour of the patient 2, substantially coincides with the current image from the analog-to-digital converter 11.

Figure 3:
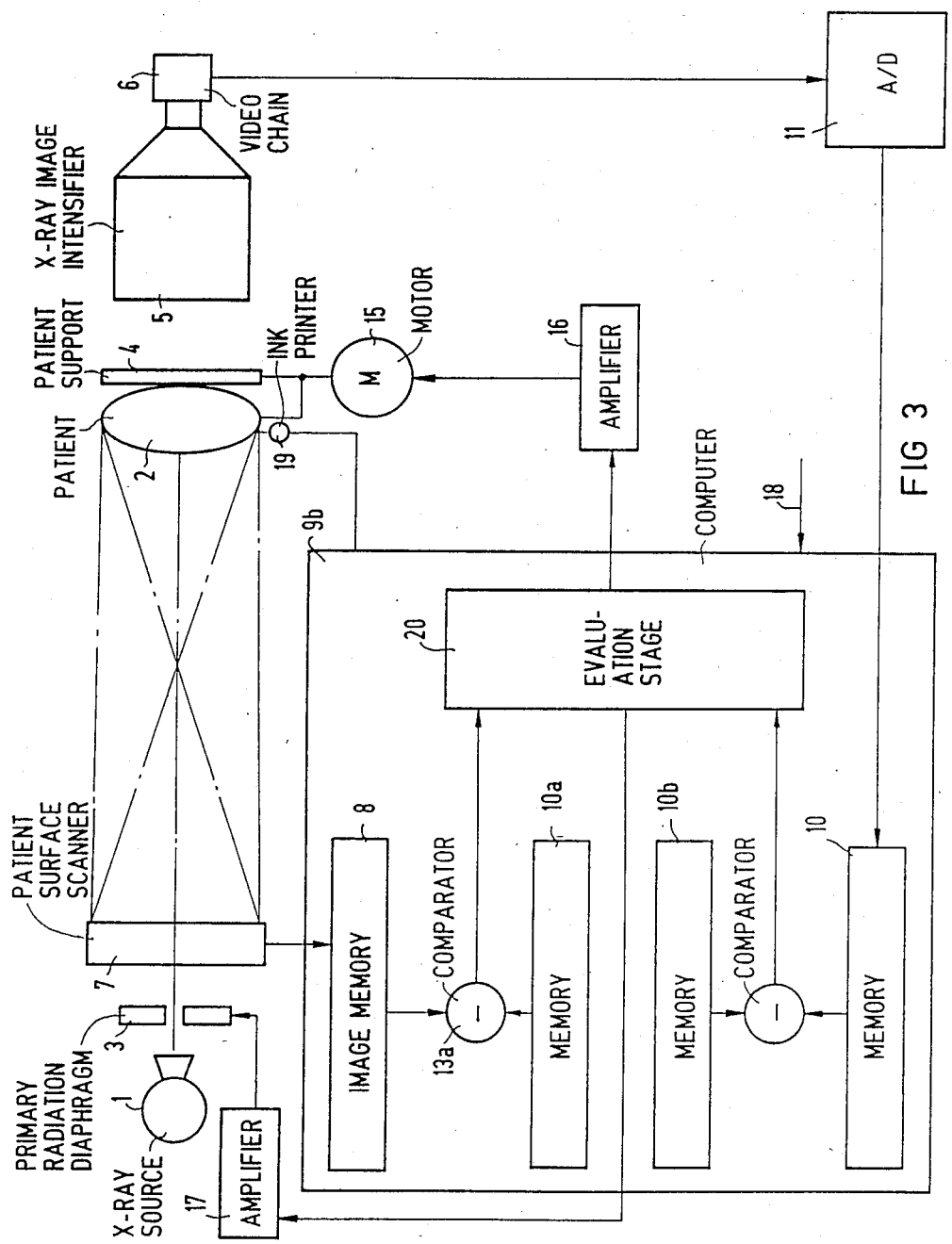
FIG. 3 is a schematic block diagram of a further embodiment of a medical examination system constructed in accordance with the principles of the present invention.

It is also possible to combine the comparison of the surface images (old and current) with the comparison of the x-ray images (old and current), as is done in the embodiment of FIG. 3. In this embodiment, a further memory 10b is provided in a computer 9b for the earlier x-ray image. The outputs of both of the comparators are supplied to an evaluation stage 20 which supplies a positioning signal for the patient support 4 via the amplifier 16 and the motor 15, and a positioning signal for the primary radiation diaphragm 3 via the amplifier 17. The evaluation stage 20 can provide a drive signal based on various evaluation criteria. For example, it can be determined in the evaluation circuit 20 which of the two comparisons has resulted in a higher correlation value, and that comparison signal is then assigned priority and is used exclusively, or primarily, to generate the positioning signal. Another possibility is to use the mean value of both comparison results. It is also possible to use different sets of criteria for generating the respective drive signals, i.e., one set for generating the patient support drive signal and another set for generating the primary radiation diaphragm drive signal. Gating of the x-ray beam is usually set on the basis of a desired x-ray attenuation value of the tissue being examined. Control of the opening of the primary radiation diaphragm 3 in the manner described above, can be undertaken by adjusting the extent to which the contour of the patient is overlapped by the radiation shadow of the primary radiation diaphragm 3.

As in the embodiment of FIG. 1, the embodiments shown in FIGS. 2 and 3 may use other image generating systems, such as a magnetic resonance imaging system or an ultrasound imaging system to generate the internal image of the patient. Any suitable type of surface scanner can be used as the surface scanner 7 in the embodiments of FIGS. 2 and 3 as well. In all of the above embodiments, the computer 9, 9a or 9b receives electrical signals at an input 18 which correspond to the apparatus geometry, which are generated in a known manner, to assist in the exact positioning of the patient 2.

The output signal from the computer 9, 9a or 9b may also be used to drive an ink printer 19 for applying markings on the patient to identify a field. Coordinates for setting the ink printer can be acquired from the image from the analog-to-digital converter 11, and from the current surface image in the image memory 8.

In addition to portraying a surface image, it is also possible in the embodiment of FIG. 1 to portray the contour of the patient 2 in a defined sectional plane or slice, for example, the section A—A shown in FIG. 1. Both the three-dimensional surface image and the contour image can be acquired by turning the surface scanner 7 relative to the patient 2.

In the embodiment of FIG. 1, the superposition of the surface image in the memory 8 with the image of the memory 10 ensues with reference to the contours of the patient 2. It is also possible to apply a suitable reference member to the patient, for example, a lead block, which is visible in both images. When superimposing the images, this reference member is then brought into coincidence in the images.

A suitable system and technique for generating the surface images, which can be used in the subject matter of the present application, is described, for example, in the periodical "Automatisierungstechnische Praxis," Vol. 2, 1988, at page 99.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical examination system for examining a patient comprising:
   means for generating an internal image of said patient, said means including an adjustable component;
   means for scanning a surface of said patient and generating a surface image of said patient;
   a memory for storing said surface image; and
   means for comparing said surface image stored in said memory with a current internal image of said patient for generating a drive signal for said adjustable component based on the difference between said stored image and said current image.

2. An examination system as claimed in claim 1 wherein said adjustable component is a patient support.

3. An examination system as claimed in claim 1 wherein said means for generating an internal image includes means for generating a radiation beam, and wherein said adjustable component is a primary radiation diaphragm disposed in said beam.

4. An examination system as claimed in claim 1 wherein said adjustable component is an ink printer for applying markings on said patient.

5. An examination system as claim in claim 1 wherein said means for generating an internal image of said is a means for generating an x-ray image of said patient.

6. An examination system as claimed in claim 1 wherein said means for scanning a surface of said patient and generating a surface image of said patient is a laser scanner.

7. A medical examination system for examining a patient comprising:
means for generating an internal image of a patient, said means including an adjustable component;
means for storing said internal image;
means for comparing a stored internal image with a current internal image and for generating a first comparison result dependent upon the correlation of the stored and current internal images;
means for scanning a surface of said patient and generating a surface image of said patient;
means for storing said surface image of said patient;
means for comparing a stored surface image with a current surface image and generating a second comparison result dependent upon the correlation between said stored and current surface images; and
means for evaluating said first and second comparison results to generate a control signal for said adjustable component.

8. A medical examination system as claimed in claim 7 wherein said adjustable component is a patient support.

9. A medical examination system as claimed in claim 7 wherein said means for generating an internal image includes means for generating an x-ray beam, and wherein said adjustable component is a primary radiation diaphragm disposed in said beam.

10. A medical examination system as claimed in claim 7 wherein said adjustable component is an ink printer for applying markings on said patient.

11. A medical examination system as claimed in claim 1 wherein said means for generating an internal image of said patient is a means for generating an x-ray image of said patient.

* * * * *